(12) United States Patent
Holbrook (10) Patent No.: US 6,767,153 B1
(45) Date of Patent: Jul. 27, 2004

(54) LOCKING POSITIONAL ARM DEVICE

(76) Inventor: Dana W. Holbrook, 103 Foxhall La., San Antonio, TX (US) 78213

( * ) Notice: Subject to any disclaimer, the term of this patent is extended or adjusted under 35 U.S.C. 154(b) by 0 days.

(21) Appl. No.: 10/361,399

(22) Filed: Feb. 10, 2003

(51) Int. Cl.[7] ................................................. F16C 11/06
(52) U.S. Cl. ............................. 403/56; 403/90; 403/76; 403/115; 403/122; 403/144
(58) Field of Search .............................. 403/56, 90, 76, 403/115, 122, 144

(56) References Cited

U.S. PATENT DOCUMENTS

| | | | |
|---|---|---|---|
| 1,829,964 A | | 11/1931 | Randall |
| 2,533,494 A | * | 12/1950 | Mitchell ....................... 403/90 |
| 3,319,982 A | | 5/1967 | Schwartz |
| 3,691,788 A | * | 9/1972 | Mazziotti ..................... 403/90 |
| 4,230,415 A | | 10/1980 | Scheerer |
| 4,974,802 A | | 12/1990 | Hendren |
| 5,020,933 A | | 6/1991 | Salvestro |
| 5,118,058 A | | 6/1992 | Richter |
| 5,544,968 A | | 8/1996 | Goellner |
| 6,343,889 B1 | | 2/2002 | Hendricks |
| 6,379,073 B1 | | 4/2002 | Yoo |
| 6,494,635 B1 | * | 12/2002 | Merlo ......................... 403/90 |

* cited by examiner

*Primary Examiner*—Lynne H. Browne
*Assistant Examiner*—Victor MacArthur
(74) *Attorney, Agent, or Firm*—Randal D. Homburg (57) ABSTRACT

A positional arm device is a series of multiple rods connected to each other by a spherical housing and ball joint with a spring-loaded locking piston providing a multiple position holding device serving as an anchor to hold tools in a certain position, and also as a connector between two object where a certain secure fixed position between the two objects is desired. The arm device has a spherical terminal rod, a plurality of intermediate rods and a terminal housing rod connected together by a spherical housing adjustably positioned and locked by a spring-loaded piston shaft engaging a sphere end retained within the housing, the piston shaft lockingly engaging one of a multiplicity of grooved indentations on the surface of the sphere end.

4 Claims, 6 Drawing Sheets

LOCKING POSITIONAL ARM DEVICE

CROSS REFERENCE TO RELATED APPLICATIONS

None

I. BACKGROUND OF THE INVENTION

1. Field of Invention

A positional arm device is a series of multiple rods connected to each other by a spherical housing and ball joint with a spring-loaded locking piston providing a multiple position holding device serving as an anchor to hold tools in a certain position, and also as a connector between two object where a certain secure fixed position between the two objects is desired. The arm device has a spherical terminal rod, a plurality of intermediate rods and a terminal housing rod connected together by a spherical housing adjustably positioned and locked by a spring-loaded piston shaft engaging a sphere end retained within the housing, the piston shaft lockingly engaging one of a multiplicity of grooved indentations on the surface of the sphere end.

2. Description of Prior Art

It is recognized that numerous devices exist that provide a multiple positioning joint for support structures, including musical instrument stands, surgical support devices, and otherwise universal connectors. Of those joints, most include a ball having a smooth surface and then another mechanism applying pressure to the surface of the ball and by mere pressure and friction, hold the ball in place within the joint. However, none of them include a thumb activated piston rod assembly that lockingly engages indentation in the ball that lock the ball in a position without rotation or movement.

The following United States patents were discovered and are disclosed within this application for utility patent. All relate to ball joint devices or multiple positioning devices. The first patent found is U.S. Pat. No. 1,829,964 to Randall which discloses a ball joint assembly having a locking mechanism allying pressure to a surface of the ball by a screw means, involving friction to the surface of the ball. Similar ball joint mechanisms are disclosed in U.S. Pat. No. 6,374,073 to Yoo, U.S. Pat. No. 6,343,889 to Headricks (also involving a split socket or housing), U.S. Pat. No. 5,544,968 to Goeliner, U.S. Pat. No. 5,020,933 to Salvestro, U.S. Pat. No. 4,974,802 to Hendron and U.S. Pat. No. 3,319,982 to Schwartz.

These devices all involve balls or spheres contained within a housing and pivot in multiple directions, and a mechanism for locking the ball or sphere within the housing, some by spring actuated means and some by a manual engaging means. However, none of these patents, singularly or in combination provide the same features, elements or characteristics of the present invention, nor does the prior art indicate the ability to perform the intended and disclosed function, utilizing the same or similar elements of the current invention.

II. SUMMARY OF THE INVENTION

Several flexible or bendable devices are present in the area of tools which allow for the positioning of an object at a certain place desired by the user, most generally to orient an object in a certain position while working on or with the object. Bending in a manner similar to a pipe cleaner, these object do hold objects in place, but none presented appear to hold an object in a secure manner where force is applied to an object. Thus, the current device, made of an assembly of different rods and housings, provides a flexible multi-positional locking arm which is conformed and configured in numerous positions and lengths to secure and hold an object clasped within a tool on the end of the device, in an intended fixed position.

Therefore, it is the primary objective of the invention to provide a multiple positioning device used with two pair of locking tools secured to each end of the device for holding an object within one of the locking tools in a certain fixed position, determined by the configuration of the device between the two locking tools.

It is also the objective of the invention to provide a device which may be used to anchor an object to a table, desk, ladder or work area in a fixed position, the object being held in such fixed position until released from the device. Depending on the composition of materials used in the device, the device may also be used to stabilize a moveable object to a stationary object to prevent movement of fall of the moveable object while working with or upon the moveable object.

III. DESCRIPTION OF THE DRAWINGS

The following drawings are submitted with this utility patent application.

FIG. 8a is inner view of a first housing component.

FIG. 8b is an inner view of a second housing component.

FIG. 9 is an exploded view of the spring-loaded piston shaft assembly.

IV. DESCRIPTION OF THE PREFERRED EMBODIMENT

Figure 1:
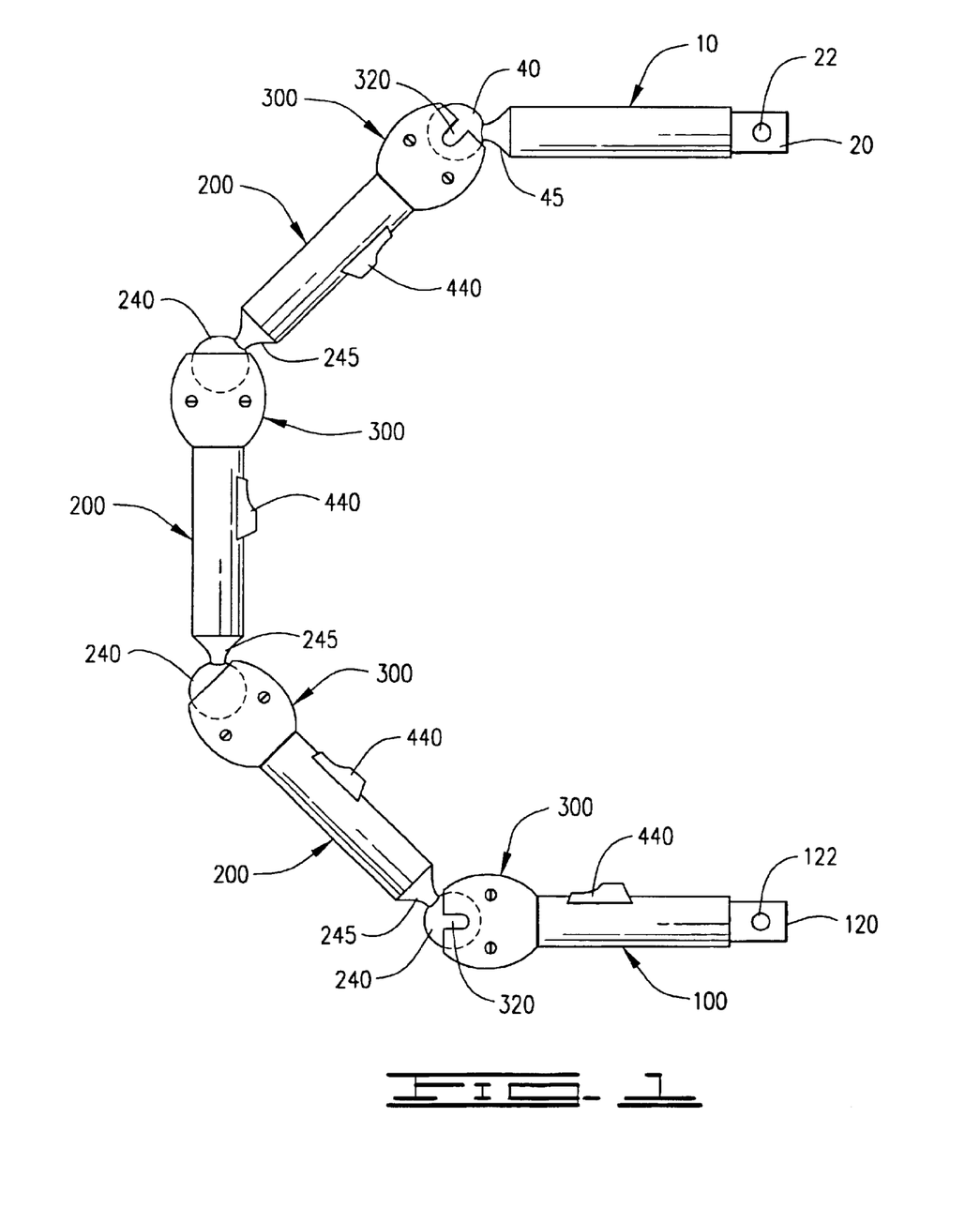
FIG. 1 is a view of the entire assembled device in a C-shape orientation.
Figure 2:
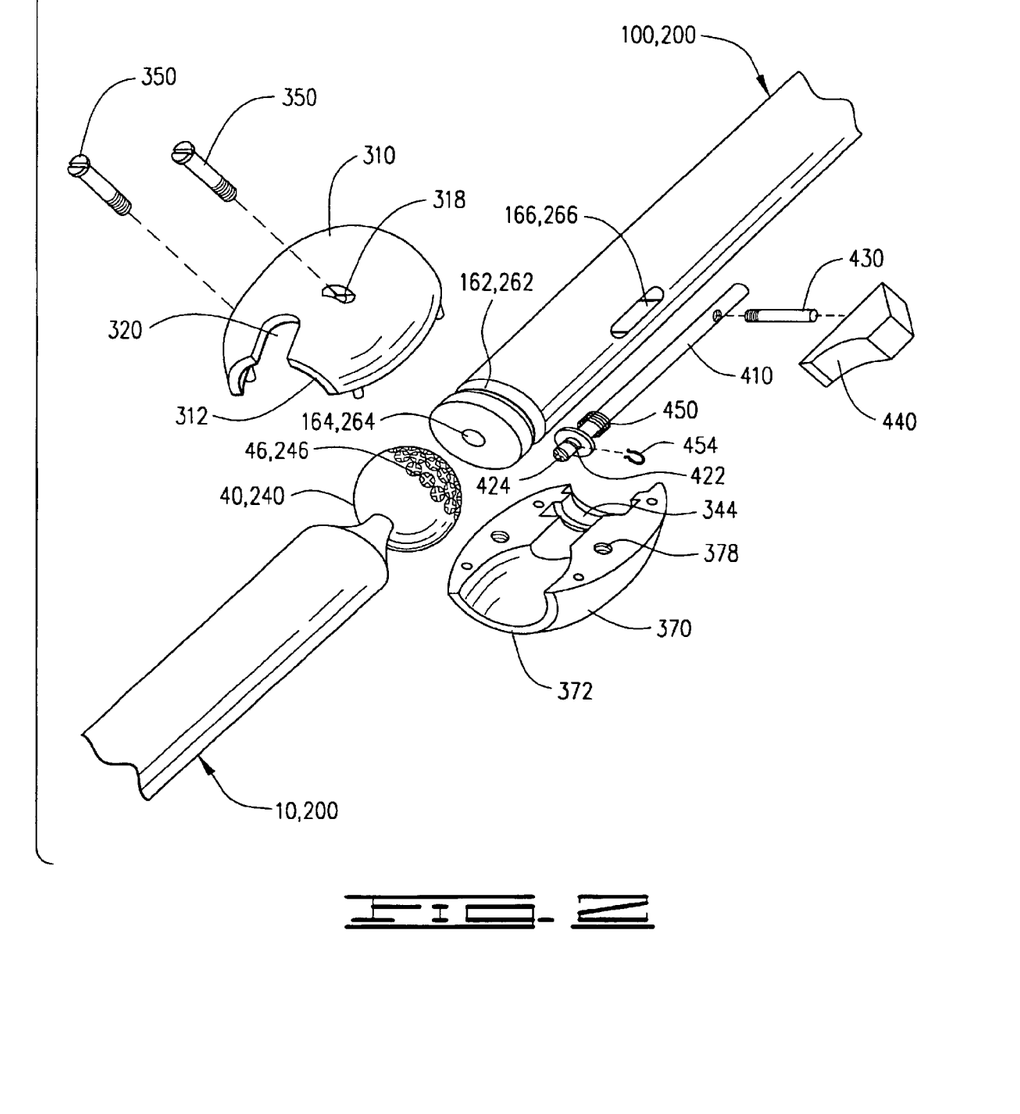
FIG. 2 is an exploded diagram of the component parts involved in a joint.
Figure 3:
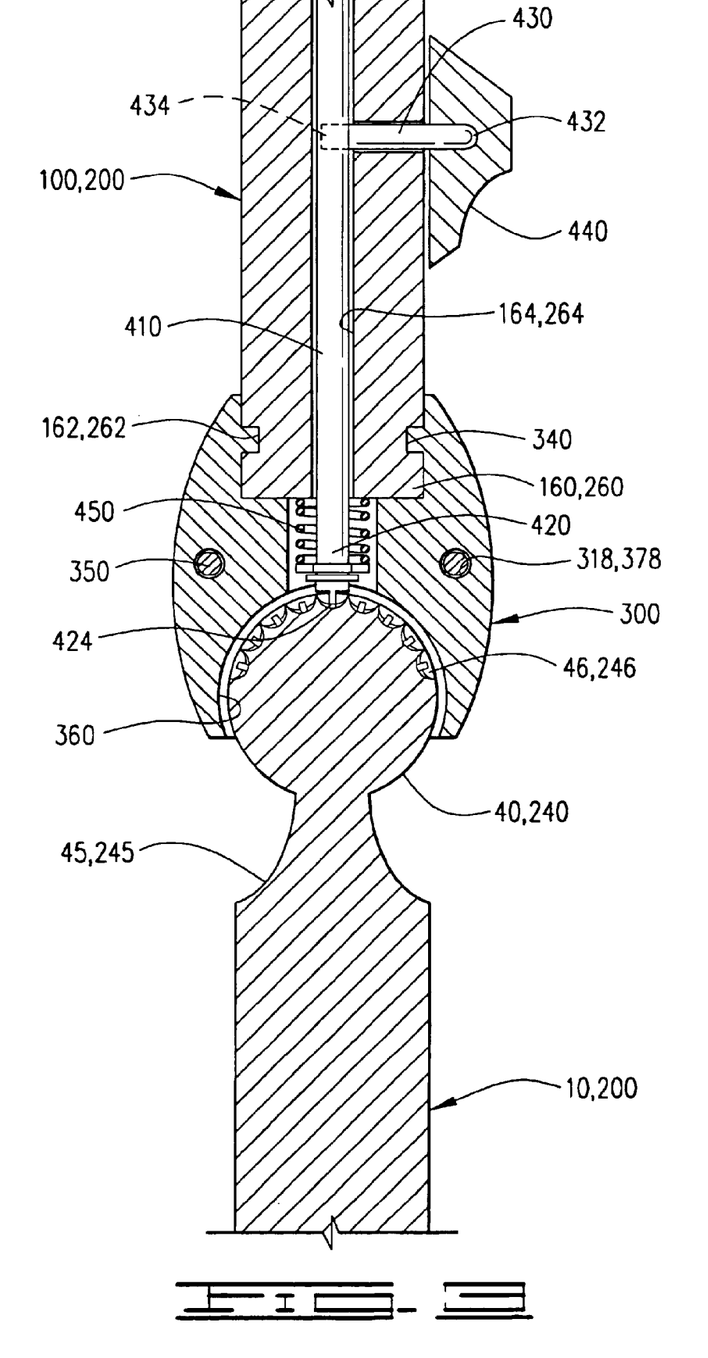
FIG. 3 is a cross section of an assembled joint
Figure 4A:
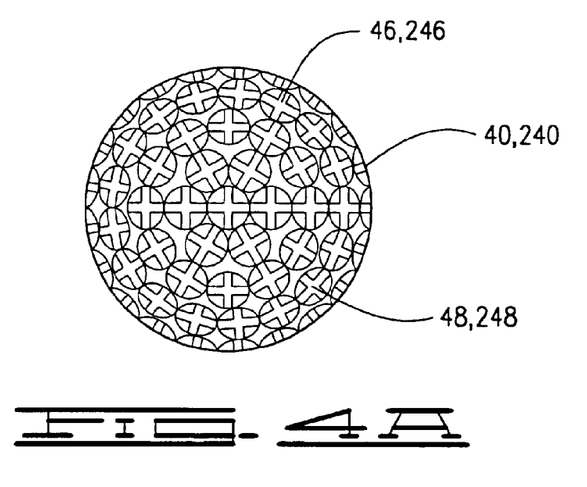
FIG. 4a is a top view of the sphere end.
Figure 4B:
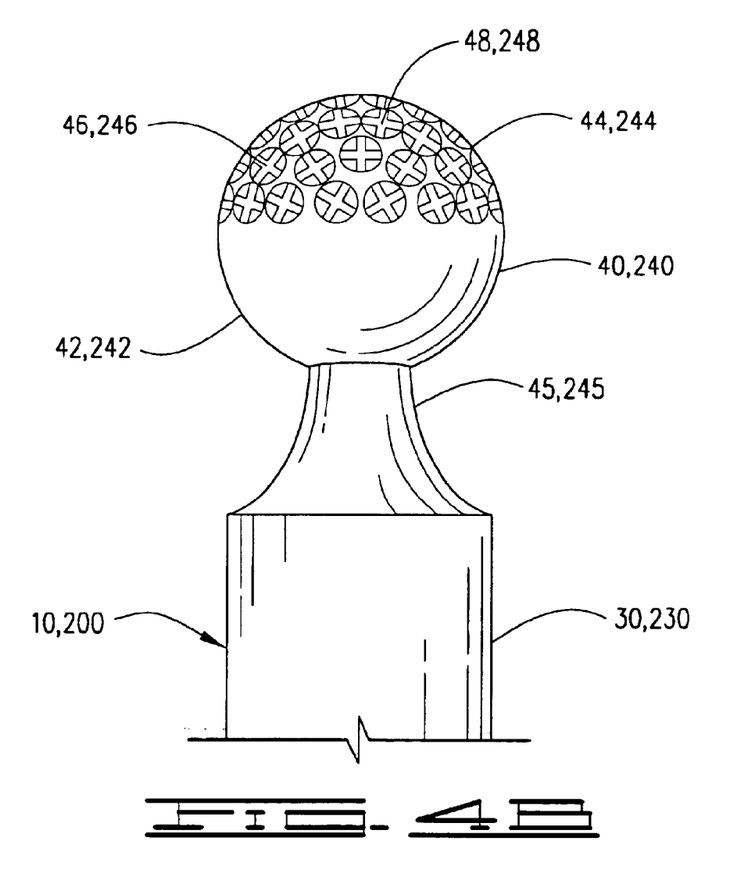
FIG. 4b is a side view of the sphere end.
Figure 5:
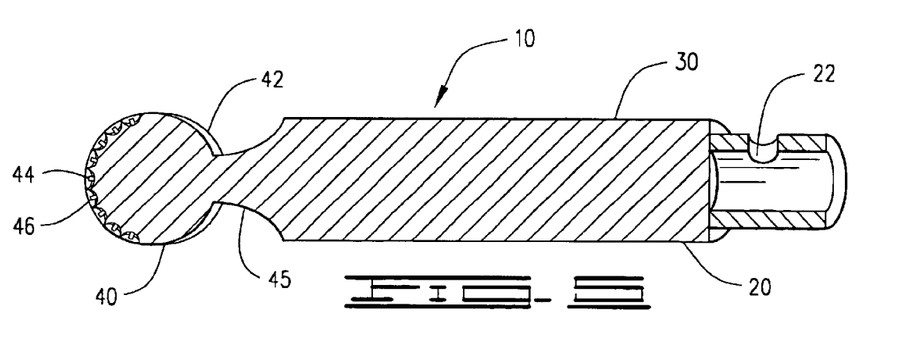
FIG. 5 is a cross section of a terminal sphere rod.
Figure 5A:
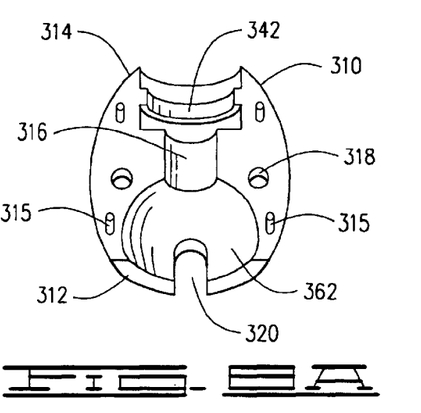
Figure 5B:
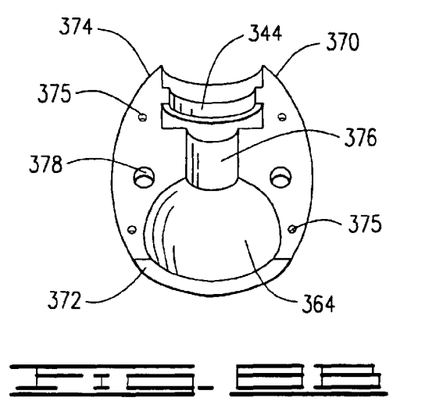
Figure 6:
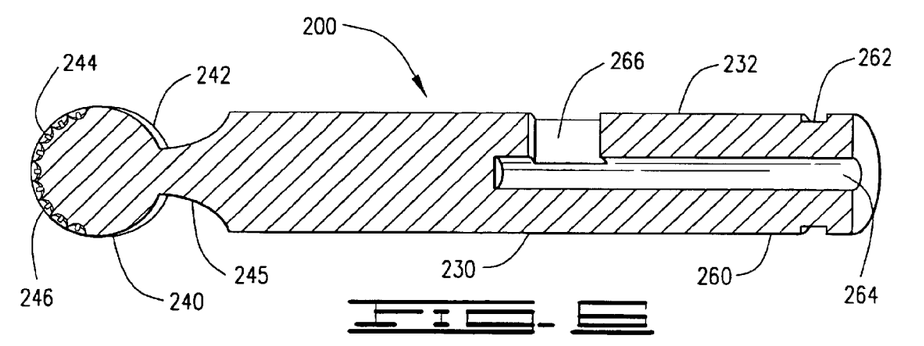
FIG. 6 is a cross section of an intermediate rod.
Figure 7:
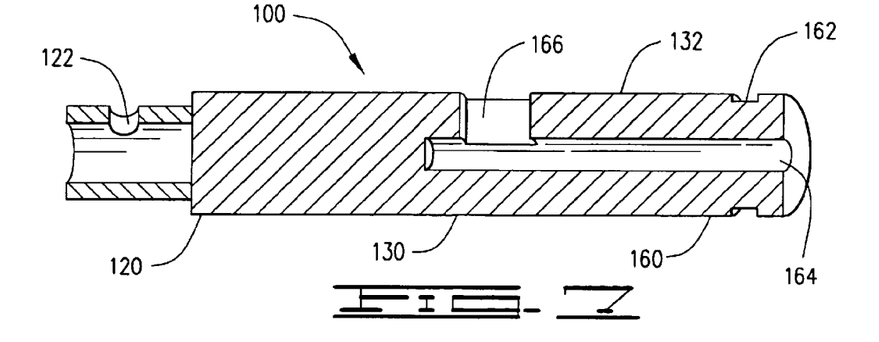
FIG. 7 is a cross section of a terminal housing rod.

A multiple adjusting support arm device, shown in FIGS. 1–9 of the drawings, attaches to two locking tools, providing an adjustable connecting arm for supporting the locking tools in a fixed position, the arm device comprising essentially a terminal sphere rod 10, FIG. 5, having a tool connecting terminal end 20, a body 30 and a sphere end 40, at least one intermediate rod 200, FIG. 6, having a sphere end 240, a body 230 and a housing end 260 forming a circular groove 262, a terminal housing rod 100, FIG. 7, having a tool connecting terminal end 120, a body 130, and housing end 160 forming a circular groove 162, a housing assembly 300, FIGS. 8a and 8b, having a first housing section 310 and a second housing section 370 attached together by screws 260, the housing assembly 300 forming a spherical cavity 360 and a circular rod engaging ridge 340, and a spring action locking piston assembly 400, FIG. 9 contained within the housing end 160, 260 of each intermediate rod 200 and terminal housing rod 100, engaging a multiplicity of grooved indentations 46, 246 on each of the sphere ends 40, 240 of the intermediate rod 200 and the terminal sphere rods 10, FIGS. 4a and 4b.

The housing assembly 300 further comprises the first housing section 310, shown in FIGS. 1–3, and 8a, said first housing section having a first hemispherical cavity 362 with an extension slot 320 at a lower end 312, a first semicircular ridge 342 at an upper end 314, said first hemispherical cavity 362 connected to the first semicircular ridge 342 by a neck channel 316, two threaded holes 318, and four mounting pegs 315. The second housing section 370, shown in FIGS. 1–3 and 8b of the drawings, further comprises a second hemispherical cavity 364 at a lower end 372, a second semicircular ridge 344 at an upper end 374, said second hemispherical cavity 364 connected to the second semicircular ridge 344 by a neck channel 376, two holes 378 and four mounting slots 375. The first housing section 310 and second housing section 370 are joined together forming the housing assembly 300 by placing the mounting pegs 315 of the first housing section within the mounting slots 375 of the second housing section, and placing one of the screws 350 through each of the two holes 378 in the second housing 370, engaging the screws 350 into the aligned threaded holes 318 of the first housing section 310, the first hemispherical cavity 362 and second hemispherical cavity 364 forming the spherical cavity 360 of the housing assembly, and the first and second semicircular ridges 342, 344 of the first housing section 310 and second housing section 370 forming the circular rod engaging ridge 340. The spherical cavity 360 captures the sphere end 240 of the intermediate rod 200 and the sphere end 40 of the terminal sphere rod 10, the spherical cavity 360 slightly larger than the sphere ends 40, 240 allowing for rotation of the sphere ends 40, 240 within the spherical cavity 360. The circular rod engaging ridge 340 engages each of the circular grooves 162, 262 on the housing ends 160, 260 of the intermediate rod 200 and the terminal housing rod 100.

The each sphere end 40, 240 of the terminal sphere rod 10 and the intermediate rod 200, more specifically shown in FIGS. 4a and 4b, include a lower section 42, 242 forming a neck 45, 245, and an upper section 44, 244 having the multiplicity of grooved indentations 46, 246. Each grooved indentation 46, 246 includes a cross grooved slot 48, 248 within said grooved indentation 46, 246. The multiplicity of grooved indentations 46, 246 covers approximately half of the respective sphere end 40, 240. The necks 45, 245 of the sphere ends extends from the housing assembly 300 when each respective sphere end 40, 240 is contained within the housing assembly 300, and the necks 45, 245 are adapted to fit within the extension slot 320 of the first housing section 310, allowing the terminal sphere rod 10 and the intermediate rod 200 to be bendable to nearly 90 degrees.

The housing end 160 of the terminal housing rod 100, FIG. 7, and the housing end 260 of the intermediate rod 200, FIG. 6, each include a partial longitudinal bore 164, 264 extending into each housing end 160, 260, each longitudinal bore 164, 264 having a perpendicular slide channel 166, 266 traversing from the longitudinal bore 164, 264 to an outer surface 132, 232 of the bodies 130, 230 of the terminal housing rod 100 and intermediate rod 200. Contained within the longitudinal bores 164, 264 and extending from the housing ends 160, 260 is the locking piston assembly 400, as shown in FIG. 3 of the drawings.

The locking piston assembly 400, shown in FIG. 9 of the drawings, includes a piston shaft 410 having a first end 412 and a second end 420, a perpendicular slide arm 430 having a slide end 432 and a threaded end 434 connecting to the first end 412 of the piston shaft 410, a thumb slide 440 connecting to the slide end 432 of the slide arm 430, and a lock channel 422 on the second end 420 of the piston shaft 410. A coil spring 450, a spring retaining washer 452 and a lock ring 454 are inserted upon the second end 420 of the piston shaft 410, the lock ring 454 securing to the lock channel 422. The second end 420 of the piston shaft 410 terminates into a convex tip 424 having a crossed locking extension 426, adapted to lockingly engage the cross grooved slots 48, 248 within any of the multiplicity of grooved indentations 46, 246 on the sphere ends 40, 240.

The locking piston assembly 400 is positioned within the intermediate rod 200 by inserting the first end 412 of the piston shaft 410 within the longitudinal bore 264, attaching the slide arm 430 to the piston rod 410 through the slide channel 266, attaching the thumb slide 440 to the slide arm 430, placing the coil spring 450 and the spring retaining washer 452 onto the second end 420 of the piston shaft 410 extending from the housing end 260 of the intermediate rod 200, and locking the coil spring 450 and spring retaining washer 452 onto the second end 420 with the lock ring 454, engaging the lock ring 454 with the lock channel 422. Placement of the locking piston assembly 400 within the terminal housing rod 100 is accomplished in the same manner.

The tool connecting terminal end 20, 120, provided on the terminal housing rod 100 and the terminal sphere rod 10, is adapted to connect to a locking tool. The tool connecting terminal end 20, 120, shown in FIGS. 5 and 7 of the drawings, may be square and supplied with a locking means 22, 122, similar in shape and function as a socket driver. In the alternative, the tool connecting terminal end 20, 120 may be a clamp or a hollow cylinder to receive a handle of a locking tool.

When assembled, as shown in FIGS. 2 and 3 of the drawings, the convex tip 424 of the second end 420 of the piston shaft 410 is oriented above the respective sphere end 40, 240 contained within the common housing assembly 300. The piston shaft 410 is urged towards the sphere end 40, 240 by the coil spring 450, and must be disengaged by pulling back on the thumb slide 440, forcing the piston shaft 410 out of the grooved indentation 46, 246 within which it is engaged at the time. With the thumb slide 440 held back, the sphere end 40, 240 is rotated within the housing assembly 300 until a desired orientation is had. At that time, the thumb slide 440 is released, and the convex tip 424 of the piston arm 410 is extended by the coil spring 450 to engage the nearest grooved indentation 46, 246 on the sphere end 40, 240, locking the sphere end 40, 240 within the housing assembly 300, and thus fixing the relative position of the intermediate rod 200 and the terminal sphere rod 10, or the intermediate rod 200 and the terminal housing rod 100.

While the invention has been particularly shown and described with reference to a preferred embodiment thereof, it will be understood by those skilled in the art that changes in form and detail may be made therein without departing from the spirit and scope of the invention.

What is claimed is:

1. A multiple adjusting support arm device attaching to locking tools, providing an adjustable connecting arm for supporting the locking tools in a fixed position, the arm device comprising:

a terminal sphere rod, having a tool connecting terminal end, a body and a sphere end;

at least one intermediate rod, having a sphere end, a body and a housing end forming a circular groove;

a terminal housing rod, having a tool connecting terminal end, a body, and housing end forming a circular groove;

a housing assembly, having a first housing section with an extension slot and a second housing section assembled by screws, the housing assembly forming a spherical cavity containing the sphere end of a terminal sphere rod or intermediate rod and a circular rod engaging ridge engaging the housing end of an intermediate rod or a terminal housing rod, said first housing section having a first hemispherical cavity with said extension slot at a lower end, a first semicircular ridge at an upper end, said first hemispherical cavity connected to said first semicircular ridge by a neck channel, two threaded holes, and four mounting pegs; said second housing section, having a second hemispherical cavity at a lower end, a second semicircular ridge at an upper end, said second hemispherical cavity connected to said second semicircular ridge by a neck channel, two holes and four mounting slots, said first housing section and said second housing section joined together forming said housing assembly by insertion of the mounting pegs of said first housing section within said mounting slots of said second housing section; and a screw inserting through each of said two holes in said second housing, engaging said screws into said aligned threaded holes of said first housing section, said first hemispherical cavity and second hemispherical cavity forming said spherical cavity of said housing assembly, and said first semicircular ridge of said first housing section and first semicircular ridge of said second housing section forming said circular rod engaging ridge, wherein said spherical cavity is adapted to accept either said sphere end of said intermediate rod or said sphere end of said terminal sphere rod, said spherical cavity slightly larger than said sphere end allowing for rotation of said sphere end within said spherical cavity and said circular rod engaging ridge engages said circular groove on either said housing end of said intermediate rod or terminal housing rod; and a spring action locking piston assembly having a convex tip including crosses locking extensions, contained within the housing end of each intermediate rod and the terminal housing rod, said locking piston assembly lockingly engaging a cross groove slot in each of a multiplicity of grooved indentations on each sphere end of the intermediate rods and the terminal sphere rods.

2. The device, as disclosed in claim 1, wherein the sphere end of each terminal sphere rod and intermediate rod further comprise:

a lower section forming a neck, said neck further connected to the body and extending from the housing assembly when the sphere end is contained within said housing assembly, said neck adapted to fit within the extension slot of the first housing section, allowing the terminal sphere rod and the intermediate rod to be positioned at an angle near 90 degrees from the housing assembly; and an upper section having the multiplicity of grooved indentations covering approximately half of the sphere end.

3. The device as disclosed in claim 1, further comprising:

the housing end of the terminal housing rod and the housing end of the intermediate rod include a partial longitudinal bore extending into the housing end, each said longitudinal bore having a perpendicular slide channel traversing from the longitudinal bore to an outer surface of the body of the terminal housing rod and intermediate rod; and the locking piston assembly contained within said longitudinal bore, said locking piston assembly further comprising:

a piston shaft having a first end and a second end, said second end of the piston shaft extending beyond the housing end terminating into the convex tip having the crossed locking extensions, adapted to lockingly engage the cross grooved slots of any of the multiplicity of grooved indentations on the sphere end of the terminal sphere rod or intermediate rod;

a perpendicular slide arm having a slide end and a threaded end connecting to the first end of the piston shaft through the slide channel;

a thumb slide connecting to the slide end of the slide arm;

a lock channel on the second end of the piston shaft;

a coil spring, a spring retaining washer and a lock ring attaching to the second end of the piston shaft, with the lock ring engaging the lock channel retaining the coil spring and spring retaining washer on the second end of the piston shaft.

4. A multiple adjusting support arm device attaching to locking tools, providing an adjustable connecting arm for supporting the locking tools in a fixed position, the arm device comprising essentially:

a terminal sphere rod, having a tool connecting terminal end, a body and a sphere end;

at least one intermediate rod, having a sphere end, a body and a housing end forming a circular groove;

a terminal housing rod, having a tool connecting terminal end, a body, and housing end forming a circular groove;

a housing assembly, having a first housing section with an extension slot and a second housing section assembled by screws, the housing assembly forming a spherical cavity containing the sphere end of the terminal sphere rod or intermediate rod and a circular rod engaging ridge engaging the housing end of the intermediate rod or the terminal housing rod; and a spring action locking piston assembly having a convex tip including crossed locking extensions, contained within the housing end of each intermediate rod and the terminal housing rod, said locking piston assembly lockingly engaging a cross grooved slot in each of a multiplicity of grooved indentations on each sphere end of the intermediate rods and the terminal sphere rods, wherein the device further comprises:

said sphere end of each terminal sphere rod and intermediate rod include an upper section having said multiplicity of grooved indentations covering approximately half of said sphere end and a lower section forming a neck, said neck further connected to the body and extending from said housing assembly when said sphere end is contained within said housing assembly, said neck adapted to fit within the extension slot of the first housing section, allowing the terminal sphere rod and the intermediate rod to be positioned at an angle near 90 degrees from said housing assembly;

said first housing section includes a first hemispherical cavity with said extension slot at a lower end, a first semicircular ridge at an upper end, said first hemispherical cavity connected to the first semicircular ridge by a neck channel, two threaded holes, and four mounting pegs;

said second housing section includes a second hemispherical cavity at a lower end, and a second semicircular ridge at an upper end, said second hemispherical cavity connected to said second semicircular ridge by a neck channel, two holes and four mounting slots, said first housing section and said second housing section joined together forming said housing assembly by insertion of said mounting pegs of the first housing section within said mounting slots of the second housing section with a screw inserting through each of the two holes in the second housing, engaging each said screw into the aligned threaded holes of the first housing section, the first hemispherical cavity and second hemispherical cavity forming the spherical cavity of the housing assembly, and the first semicircular ridge of the first housing section and the second semicircular ridge of the second housing section forming the circular rod engaging ridge, wherein the spherical cavity is adapted to accept either the sphere end of the intermediate rod or the sphere end of the terminal sphere rod, the spherical cavity slightly larger than said sphere end allowing for rotation of said sphere end within said spherical cavity and said circular rod engaging ridge engages the circular groove on either the housing end of the intermediate rod or terminal housing rod;

said housing end of the terminal housing rod and said housing end of the intermediate rod include a partial longitudinal bore extending into said housing end, each said longitudinal bore having a perpendicular slide channel traversing from said longitudinal bore to an outer surface of the body of the terminal housing rod and intermediate rod; and said locking piston assembly contained within said longitudinal bore, including:
  a piston shaft having a first end and a second end, said second end of said piston shaft extending beyond the housing end terminating into the convex tip having the crossed locking extensions, adapted to lockingly engage the cross grooved slots of any of the multiplicity of grooved indentations on the sphere end of the terminal sphere rod or intermediate rod;
  a perpendicular slide arm having a slide end and a threaded end connecting to the first end of the piston shaft through the slide channel;
  a thumb slide connecting to said slide end of said slide arm;
  a lock channel on said second end of said piston shaft;
  a coil spring, a spring retaining washer and a lock ring attaching to said second end of said piston shaft, with said lock ring engaging said lock channel retaining said coil spring and spring retaining washer on said second end of said piston shaft.

* * * * *